United States Patent [19]
Burkhart

[11] Patent Number: 5,330,468
[45] Date of Patent: Jul. 19, 1994

[54] DRILL GUIDE DEVICE FOR ARTHROSCOPIC SURGERY

[76] Inventor: Stephen S. Burkhart, 201 Village Cir., San Antonio, Tex. 78232

[21] Appl. No.: 134,983
[22] Filed: Oct. 12, 1993
[51] Int. Cl.$^5$ ............................................. A61F 5/04
[52] U.S. Cl. ................................................... 606/96
[58] Field of Search ...................... 606/87, 88, 89, 96, 606/103, 104

[56] References Cited

U.S. PATENT DOCUMENTS 4,672,957  6/1987  Hourahane ........................... 606/96

FOREIGN PATENT DOCUMENTS

1217372  3/1986  U.S.S.R. ................................. 606/87

Primary Examiner—Tamara L. Graysay
Attorney, Agent, or Firm—Gunn, Lee & Miller

[57] ABSTRACT

A drill guide device for drilling straight tunnels through bone, the drill guide device having a hollow aiming tube with a curved end and a hollow receiving tube with a curved end. The aiming tube and the receiving tube are both attached to a curved frame for allowing angular adjustment between the aiming device and the receiving device. A rotating pin is inserted through the aiming tube, passes through the curved end and drills a straight tunnel through the bone where it is received into the receiving tube. The receiving tube forces the needle to curve rather than continuing on its straight path as determined by the tunnel through the bone. The curved aiming and receiving tubes allow a surgeon to work in an area which is "boxed in" by nerves, bones or the like which thereby would not allow the use of a straight drill guide.

17 Claims, 5 Drawing Sheets

DRILL GUIDE DEVICE FOR ARTHROSCOPIC SURGERY

FIELD OF THE INVENTION

This invention relates to an orthopedic drill guide, specifically an orthopedic drill guide having a hollow curved aiming device for insertion of a flexible drill bit there through.

BACKGROUND

Typically, tissue repair to the shoulder area, such as reattaching torn rotator cuff tendons to bone, is done through open surgery. However, open surgery introduces potential problems with the trauma associated with the large area of skin, muscle and tissue which must be incised to perform such surgery.

Arthroscopic surgery has the advantages of making a small incision and therefore reducing the risk of infection, blood loss and the like which is sometimes the result of open surgery. However, arthroscopic repair of the rotator cuff through bone tunnels has not been performed, a result of, among other things, lacking the necessary instruments. For example, in attaching the rotator cuff to the humerus by suturing the tendon to the bone by passing the suture through a hole drilled through the proximal portion of the humerus, specific problems arise. Just distal to the bone tunnel site lies the axillary nerve, a major nerve which innervates the deltoid muscle. If the axillary nerve is damaged, movement of the shoulder may be impaired. Proximal to the humerus is the acromion. Thus, the location at which the tunnel is to be drilled is effectively "boxed in". This prevents the use of straight pins to bore the hole.

Applicant has provided an instrument which allows drilling a straight hole through bone in an area bordered by obstacles. Applicant has provided a device in which straight holes can be drilled in bones through the use of a flexible pin, such as a Nitinol pin, used in conjunction with a curved, tubular aiming device, and a curved tubular receiving device. Moreover, since the acromion may be different lengths in different individuals, there is needed some adjustability to the drilling device. Orthopedic drill guide devices are known in the art. For example U.S. Pat. No. 4,945,904 (Bolton, et al 1990) discloses an orthopedic drill guide device used to locate and guide the drilling of holes in bones for the purpose of implanting tissue repair devices. Specifically, the Bolton drill guide device is designed to locate, align and guide the drilling of a tibial through-hole and then to locate, align and guide the drilling of the femoral through-hole with respect the previous drilled tibial through hole. The Bolton device would be incapable of use arthroscopically for shoulder work such as reattaching torn rotator cuffs. The Bolton device, like other prior art devices, provides a device wherein the longitudinal axis of the drill guide aiming device is designed to align with the longitudinal axis of the hole which is intended to be drilled. Applicant, on the other hand, cannot use such a device because of the proximity of the axillary nerve and the acromion to the drill site.

Another prior art device for use as a drill guide is disclosed in U.S. Pat. No. 5,112,337 (Paulos, et al 1992). The Paulos patent discloses another straight tubular drill guide aiming device for alignment with the longitudinal axis of the tunnel to be drilled. Specifically, the Paulos drill guide is designed for drilling a tunnel in the tibia for anterior cruciate ligament reconstruction. The drill guide aiming device is used in conjunction with a target hook having a point for engaging and determining the exit point of the tunnel. The shortcomings of this device with respect to arthroscopic shoulder surgery are the same as Bolton, both require the use of a straight tubular aiming device with longitudinal axis coincident with the longitudinal axis of the tunnel to be drilled.

Thus, applicant's device provides for the use of a curved aiming device, tubular for receipt of a flexible pin, for alignment adjacent an entry point and drilling a straight tunnel through proximal end of the humerus, while avoiding exposure of the axillary nerve to the instrument. Applicant also provides for a curved tubular receiving device which avoids interference between the pin and the acromion. Thus, applicant provides an orthopedic drill guide device for use in drilling a straight tunnel through bone where obstructions prevent the use of straight drill aiming and receiving devices.

DETAILED DESCRIPTION OF THE PREFERRED EMBODIMENTS

FIGS. 1-4A illustrate various views showing the main components of applicant's drill guide (10). Drill guide (10) is seen to comprise a curved frame (12) having a rectangular cross section (see also FIG. 4A) and a constant radius of curvature. Attached to one end of frame (12) is aiming device (14). Slidably attached to frame (12) is receiving device (16), movable with respect to aiming device (14).

Aiming device (14) is comprised of hollow tube (18) having a removed curved end (20). Tube (18) is dimensioned sufficiently to enable the passage of pin (26) therethrough. Pin (26) is designed to enter tube (18) at straight end (24) through straight end opening (25). Pin (26) passes through straight portion (22) of tube (18), through curved end (20) and out pin opening (21) (see also FIGS. 2 and 2A). Pin (26) is typically Nitinol and has a loop (28) at one end thereof for passing a suture therethrough. Tip (30) is located at the other end of pin (26) for puncturing the cortex of the humerus and creating the tunnel through the bone (see FIG. 1). Aiming device (14) is mounted to frame (12) by mounting means (27) as more specifically set forth in detail below.

It can be seen then that aiming device (14) is capable of receiving pin (26) that is flexible enough so it can change direction from straight portion (22) at curved end (20) which curved end is placed adjacent to the cortex of proximal humerus as more specifically set forth below. This change in direction occurs as pin (26) is urged through tube (18) and tip (30) strikes the walls of bore (23) as tip approaches and passes through curved end (20). Receiving device (16) is designed to capture tip (30) of pin (26) as it exits the cortex of the proximal humerus and before it reaches the acromion. This is done by providing receiving device (16) with a tube (32) of dimension similar to that of tube (18) of aiming device (14). Tube (32) of receiving device (16) has straight portion (34) and a curved end (36). Curved end (36) captures pin (26) as it exits the cortex of the humerus and redirects flexible pin (26) along straight portion (34) thereof.

Figure 1:
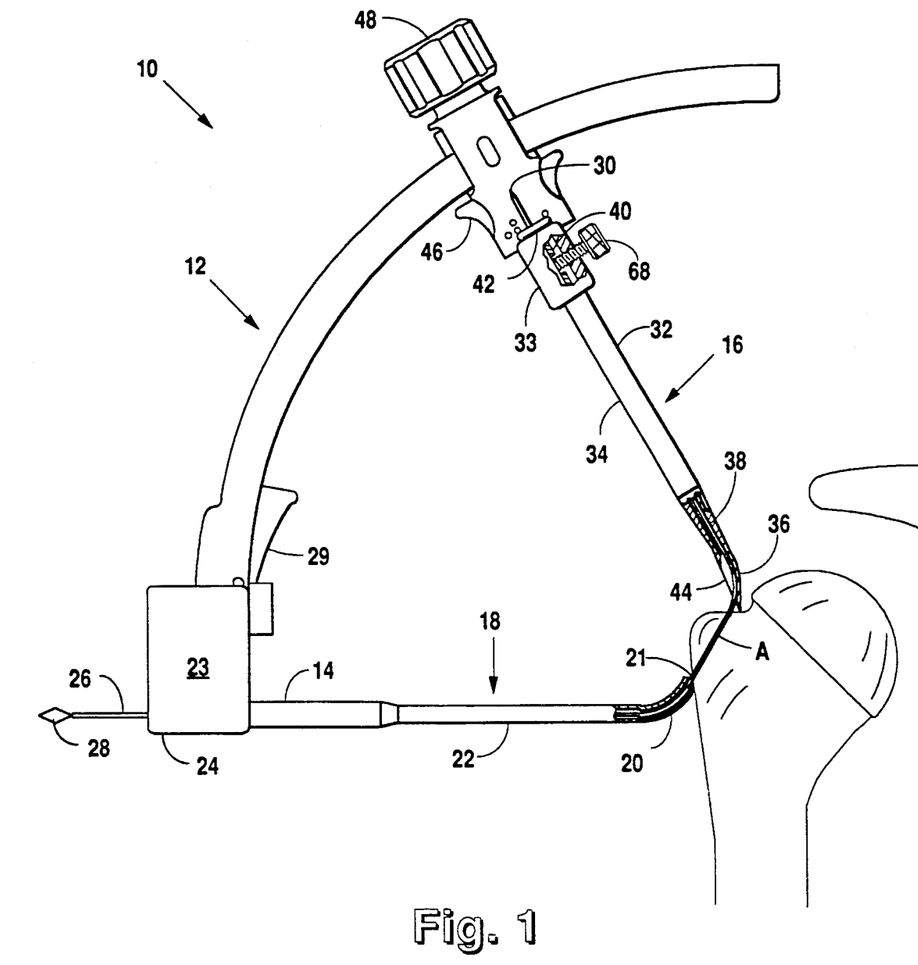
FIG. 1 is an elevational view of drill guide 10 with aiming and recovery means in place against proximal end of the humerus illustrating generally the position of the device in use.
Figure 1A:
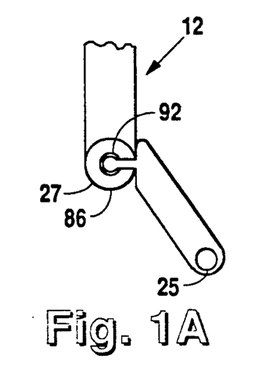
FIG. 1A is a top elevational view of the aiming device of applicant's invention attached to the frame.

As can be seen in FIG. 1 pin (26) is capable of extending through bore (38) and out straight end (40) through straight end opening (42). That is, pin (26) changes direction between the axis of the hole drilled in the humerus (see FIG. 1) and the axis of straight portion (34). This change of direction occurs at curved end (36) as pin (26) enters pin opening (44) and engages the walls of bore (38). Such a change in direction is necessary to prevent interference between pin (26) and the acromion.

As seen in FIG. 1 attachment means (33) provides means for adjustably attaching receiving device (16) to frame (12) in a manner more specifically set forth below and with reference to FIGS. 3-4A. Release means (46) allows receiving device (16) to be removed from adjustment means (48). Adjustment means (48) allows receiving device (16) to be adjustably set at a variety of angles with respect to aiming device (14). This adjustment is provided to accommodate different size individuals. For example, with some individuals, the acromion may not reach as far as illustrated in FIG. 1 or may reach further distally than illustrated in FIG. 1 and thus require a more narrow angle between aiming device (14) and receiving device (16).

Figure 2:
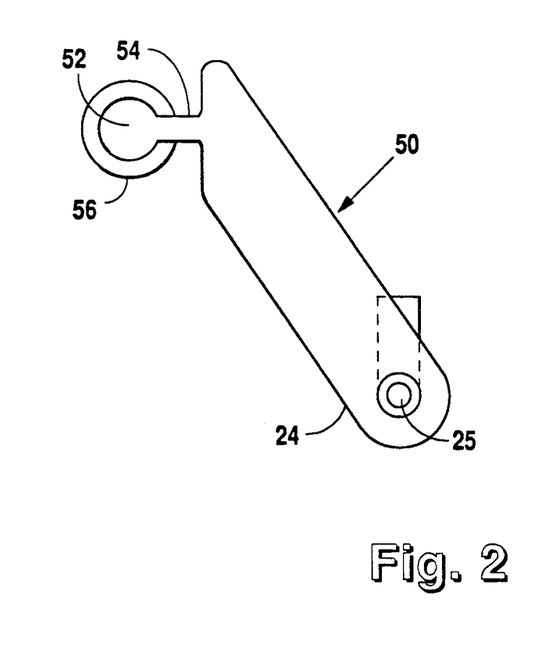
FIGS. 2, 2A and 2B are elevational views illustrating details of the aiming device of applicant's invention.
Figure 2A:
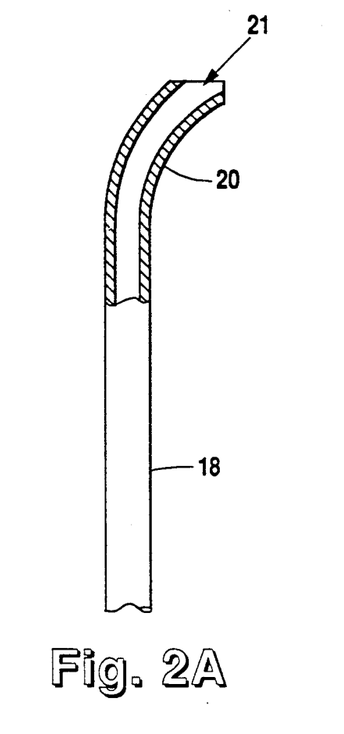
Figure 2B:
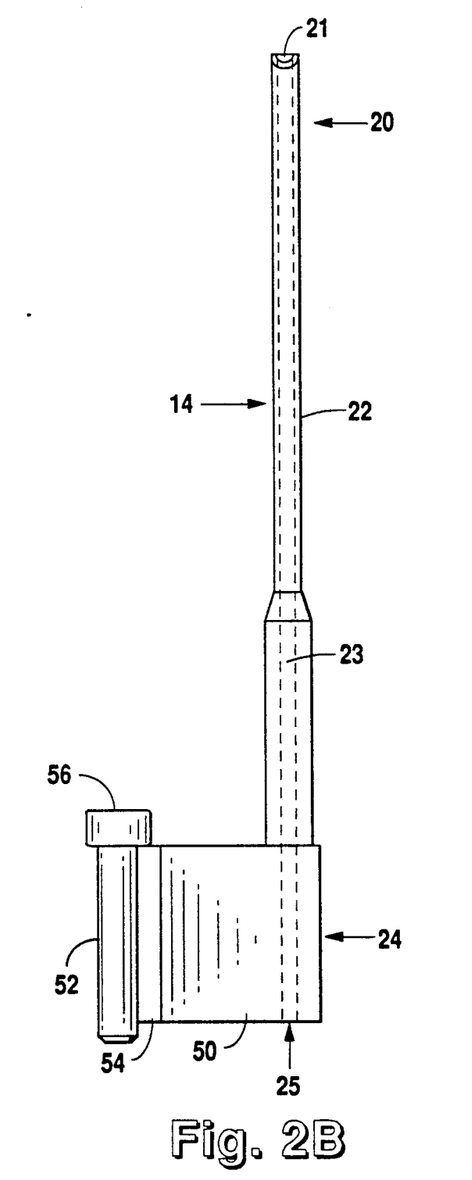

Turning now to details of aiming device (14) and with reference to FIGS. 2-2B, it is noted that aiming device (14) is comprised of rectangular standoff (50) which functions to set tube (18) in a plane outside of but parallel to the plane created by curved frame (12). This offset matches a similar offset of receiving device (16) and is found to be more convenient to manufacturer and use as compared to having no offset. At the distal end of standoff (50) is located shaft (52) which is cylindrical in nature having a longitude axis parallel to that of straight portion (22) of tube (18). Shaft (52) is attached to standoff by tabular ridge (54). The dimensions of shaft (52) and ridge (54) as well as stop (56) are designed for slidable receipt into mounting means (27) as more particularly set forth below with reference to FIGS. 4 and 1A.

FIGS. 2-2B help illustrate the design of curved end (20) of tube (18). More specifically, it is seen with reference to FIG. 2A that curved end (20) has pin opening (21) that is beveled with respect to axis (A) (see FIG. 1). Axis (A) is the axis of pin (26) as it emerges from pin opening (21) and curved end (20) and also defines the axis of the tunnel or hole drilled in the humerus as illustrated in FIG. 1. This beveled tip of curved end (20) is provided to keep pin (26) in contact as long as possible with the walls of pin opening (21) until contact between tip (30) of pin (26) and the cortex of the bone to be drilled. That is, as tip (30) of pin (26), which is rotating at a high speed as it merges from pin opening (21), strikes the cortex of the humerus it will attempt to "ride up" to the top of pin opening (21) as viewed in FIG. 2. For as true an axis as possible, therefore, opening (21) has walls beveled to maintain curved end (20) in contact with pin (26) and minimize the free space between curved end (20) and the cortex of the bone to be drilled.

Figure 3:
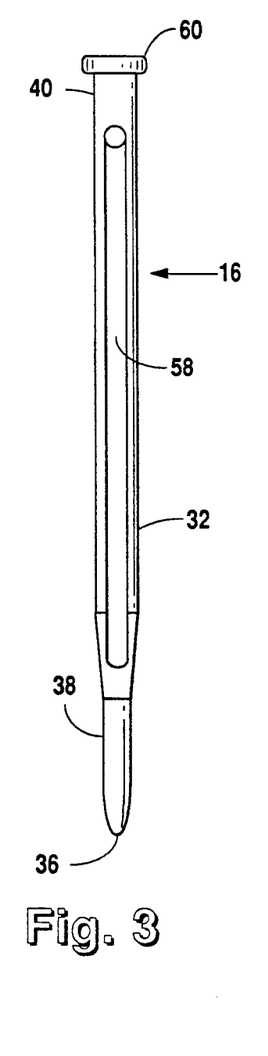
FIGS. 3, 3A, 3B, 3C and 3D are various elevational views illustrating details of the receiving device of applicant's invention showing tube (32) detached from attachment means (33) (FIG. 3.)
Figure 3A:
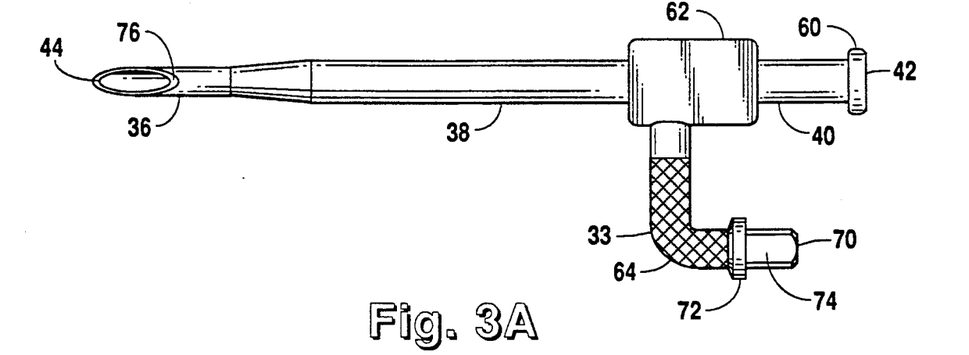
Figure 3B:
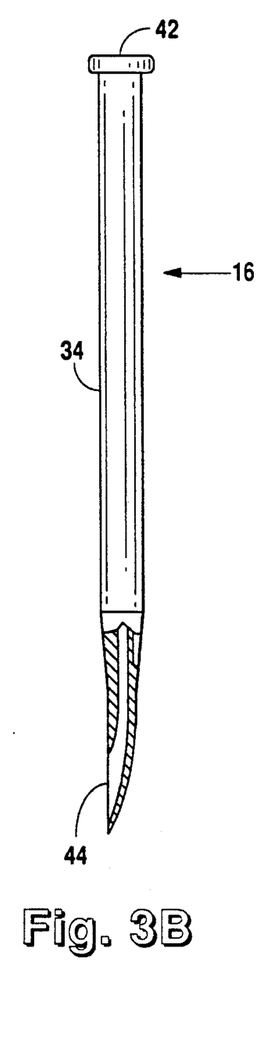
Figure 3C:
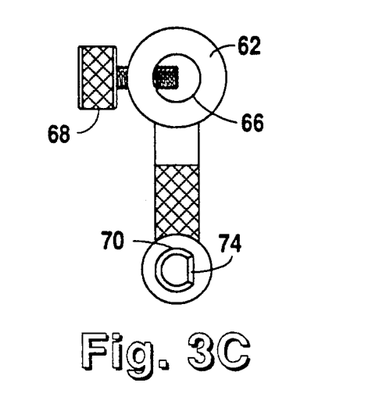
Figure 3D:
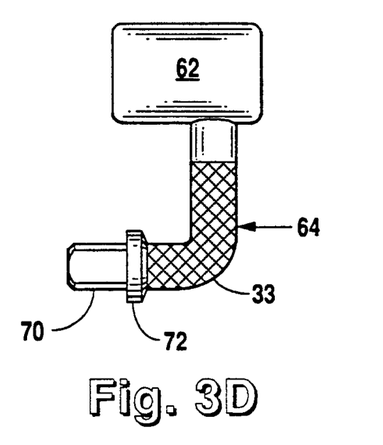

Turning now to FIGS. 3-3D and the details of receiving device (16), it is seen that receiving device (16) has walls defining a groove (58) in the outer walls of straight portion (34) thereof. A stop collar (60) is located at the terminus of straight end (40) of tube (32) adjacent straight end opening (42). Receiving device (16) is comprised of tube (32) engageable with a cylindrical mounting member (62). The cylindrical mounting member (62) has a standoff arm (64) to hold tube (32) adjacent the plane of frame (12), the same distance therefrom that standoff (50) provides for aiming device (14). Standoff arm (64) is attached to cylindrical mounting member (62), the latter having a bore (66) therethrough for receipt of tube (32) therethrough. A thumbscrew (68) is threaded through cylindrical member (62) which has bore (66) just slightly larger than diameter of tube (32) such that groove (58) faces the removed end of thumbscrew (68). This allows tube (32) of receiving device (16) to be adjustably set with different lengths with respect to the distance between pin opening (44) of curve (36) and frame (12). This is effected by sliding tube (32) through bore (66) until the required length is reached and then tightening thumbscrew (68) against groove (58). This adjustment is provided to accommodate typical anatomical differences between various individuals.

At removed end of standoff arm (64) opposite cylindrical mounting member (62) is found insert stub (70) with locking collar (72) at one end thereof. Insert stub (70) is designed for receipt into adjustment means (48) at release means (46) as more specifically set forth below with reference to FIGS. 3, 3A and 4. Insert stub (70) is generally cylindrical with the exception of having a portion of its circumference defining flat side (74) as seen in FIGS. 3A and 3C. Flat side (74) will engage release means (46) to maintain a fixed angular relationship between standoff arm (64) and frame (12).

FIG. 3A also illustrates walls (76) of pin opening (44) of receiving device (16). As seen in FIG. 3A of walls (76) will be generally parallel to the plane of the longitudinal and axis of straight portion (34) tube (32). This provides for a sufficiently large, oval shaped, pin opening (44) and therefore ease of receipt of, and a greater likelihood of capturing, pin (26) as tip (30) emerges from the cortex of the tunnel drilled in the bone. Reference to FIG. 1 also illustrates the passage of pin (26) through the tunnel as it is captured by receiving device (16) and redirected by interference between tip (30) and walls of bore (38) to align with axis of straight portion (34) of tube (32). The net effect of providing curved end (20) to aiming device (14) and curved end (36) to receiving device (16) is to, when used in conjunction with flexible rotating pin (26), provide for a means of drilling a straight hole through a bone in a confined space such as that illustrated in FIG. 1.

Figure 4:
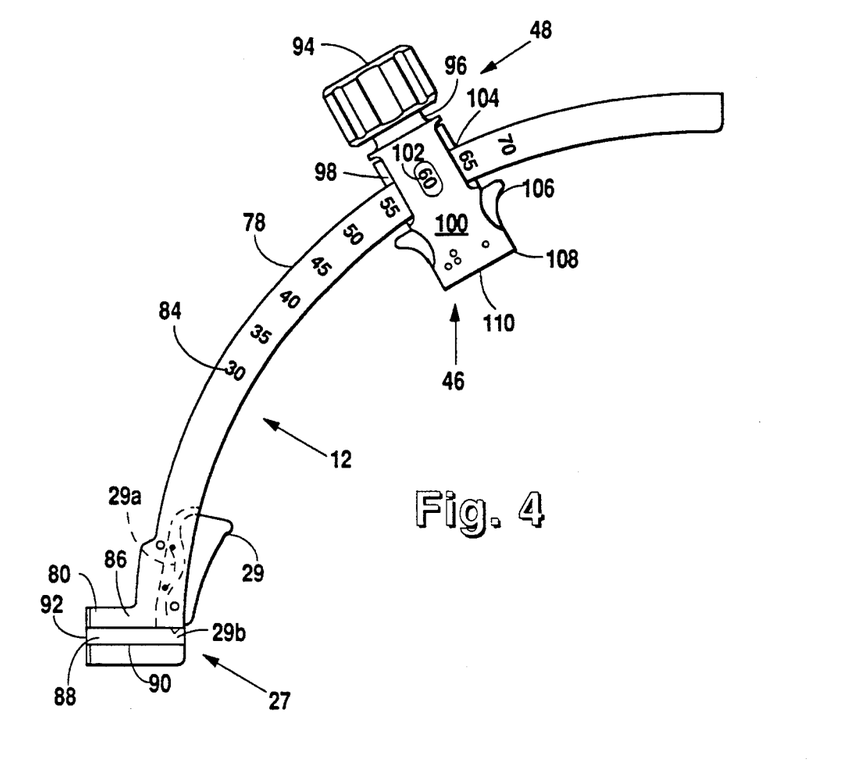
FIG. 4 is an elevational view of the frame of applicant's present invention with aiming device and receiving device removed therefrom.

Turning now to FIG. 4 and with reference to all of the preceding figures the structure used as drill guide (10) can be appreciated. Specifically, FIG. 4 illustrates curved frame (12) having generally rectangular body (78) with indicia (84) on the walls thereof. The indicia are markings denoting the interior angle between the axes of straight portion (22) of tube (18) and straight portion (34) tube (32).

Body (78) has near end (80) on which is attached aiming device (14) by mounting member (27). Removed end (82) is provided having the same general, typically rectangular, cross sectional shape as body (78). This is to accommodate the receipt of adjustment means (48) onto removed end (82).

Turning now to near end (80) it is seen that a cylindrical boss (86) is integral with body (78) at near end (80). Boss (86) has a slot (88) therein, slot (88) defines a channel leading to a bore (92). With reference now to FIG. 2 it is seen that shaft (52) will slide snugly into bore (92) up to stop (56). Moreover it is seen that channel (90) of slot (88) will fit snugly adjacent ridge (54) to maintain a fixed angular orientation of standoff (50) with respect to the plane of frame (12). Release means (29) is designed to accommodate the fingers of the hand such that when depressed it will release friction locking holding shaft (52) in a fixed position within bore (92). Thus, while stop (56) is typically resting against frame (12) with shaft (52) within bore (92), depressing release means (29) will release friction break against shaft (52) and allow aiming device (14) to either slide fully out of bore (92) or to fix tube (18) at a selective distance between pin opening (21) and frame (12). Release means (29) has edge (29b) that is urged by leaf spring (29a) against walls of shaft (52).

Turning now to the details of adjustment means (48) and with reference to FIGS. 2 and 4 it is seen that adjustment means (48) comprises knob (94) having a surface knurled for ease of rotation. Attached to knob (94) is threaded shaft (96), having a removed end acting against a disc (98). Rotation of knob (94) will urge the removed end (96a) of shaft (96) against disc (98) to act as a friction break locating adjustment means (48) at a selectively fixed angular relationship about frame (12) with respect to receiving device (14). It can be seen then with reference to FIG. 4 that adjustment means (48) is comprised of body (100) having walls defining window (102) adjacent walls of frame (12) allowing the viewing of indicia (84) therethrough. Central opening (104) in body (100) typically matches the rectangular cross sectional shape of frame (12) with the exception of being sufficiently large to accept disc (98) adjacent removed end (96a) of threaded shaft (96) and fixed sliding puck (99), typically plastic and notched for sliding within walls (105) of frame (12) (see FIG. 4A) thus, tightening down knob (94) will urge disc (98) against walls of frame (12). This in turn will urge puck (99) against opposite walls (105) of frame (12) to prevent adjustment means (48) from sliding over frame (12). Disc (98) and puck (99) are typically made of a polymer of tetraflouraethyline sold under the trademark TEFLON or plastic material.

Figure 4A:
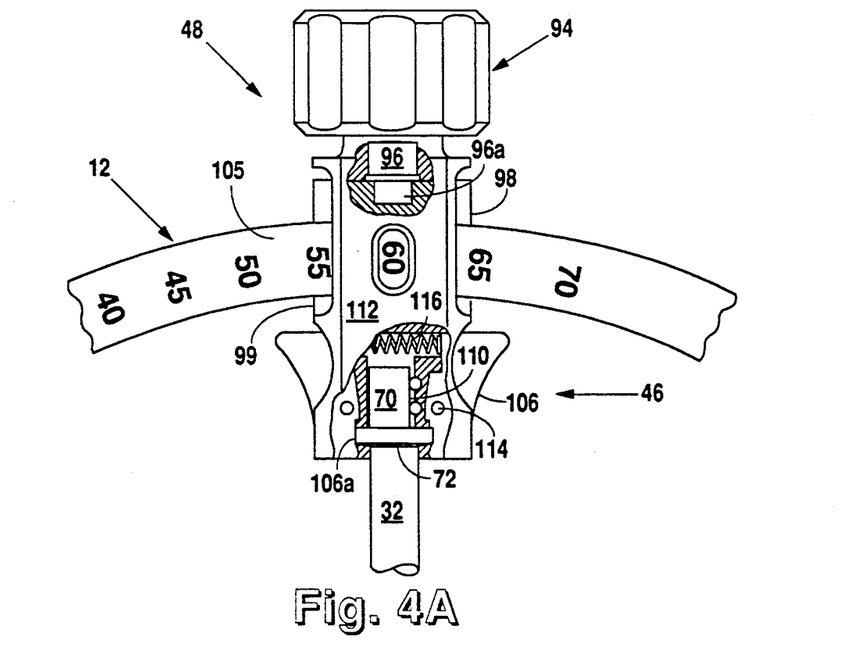
FIG. 4A is an elevational cross sectional cutaway view through the adjustment means of the drill guide and a partial cross sectional view through the release means of the drill guide with receiving device (16) in place.

Noting the details of structure of release means (48) it is seen with reference to FIG. 4 that collar grips (106) have notch portion (106a) which will engage locking collar (72) of receiving device (14) when insert stub (70) is inserted into stub shaft (110) (see FIG. 4A).

Method in which release means (46) operates to maintain receiving device (16) to frame (12) is set forth in FIGS. 4 and 4A. More specifically, FIG. 4A illustrates release means (46) having body (112) into which is pivotally engaged on pins (114) collar grips (106). It is seen that spring (116) maintains collar grips (106) in a spread or outward position of the gripping portions thereof and keeps notch portion (106a) in a closed or engaged position. Thus, receipt of insert stub (70) into stub shaft (110) until locking collar (72) engages the walls thereof, while collar grips (106) are depressed and notch portions (106a) are in a split apart or spread position will, upon releasing collar grips allow notch portions (106a) to engage and hold locking collar (72). The location of notch portions (106a) and walls of body (112) engage locking collar (72) to prevent receiving device (16) from falling out of release means (46).

Thus, it is seen how use of frame (12) with adjustably mounted receiving device (16) and aiming device (14) provides for drill guide (10) which is adjustable and further provides for a device capable of drilling a tunnel or hole through bone along an axis non-parallel with that of the aiming and receiving device.

The drill guide of applicant's present device is intended to be used for any suitable arthroscopic surgery. For example, the device may be used for arthroscopic surgery to the shoulder, specifically, to reattach a torn rotator cuff tendon to the proximal end of the humerus. Briefly, the procedure of such use is as follows.

The surgeon locates the edge of the acromion. Approximately 5 cm. below that is the transverse trending axillary nerve. The puncture 6 to 8 mm. in length is incised in the skin about 4 cm. below the acromion for insertion of the aiming device. The arthroscope has been previously inserted for viewing the drill site. The aiming device is inserted until the aiming tube opening rests adjacent to the entry site of the tunnel to be drilled, and above the axillary nerve, against the cortex of the bone. Typically, the drill will enter from the lateral cortex of the proximal humerus and exit close to the junction of the articular surface of the proximal humerus and the greater tuberosity. The axial position of the receiving device is adjusted to clear the distal end of the acromion. This positioning is accomplished by loosening the adjustment knob moving the adjustment means to the desired location and tightening the knob. A puncture wound 6 to 8 mm. in length is made for insertion of the tube of the receiving device. The receiving tube should clear the acromion and lay against the cortex at the exit point. Final adjustments of curved ends (20) and (36) are made to position them adjacent to humerus. With the frame secured with respect to the patient and the humerus immobilized, a Nitinol pin is placed in a drill, the drill is started and inserted into the tube of the aiming device. A tunnel is drilled through the proximal humerus between the entrance and exit points adjacent the curved ends.

When the tip of the pin breaks through the exit point, the surgeon, depending upon the stitching method chosen, may pass a length of suture through the loop and pull the pin through aiming device (14), through the tunnel drilled, until the loop clears the exit point of the tunnel. The surgeon may then withdraw the suture from the loop and slide the pin the rest of the way through tube out of opening. Through the use of knot grabbers and knot pushers the suture ends may be manipulated as desired by the surgeon to reattach the tendon, such as by passing the suture material through the tendon and the tunnel created in the humerus and securing the torn rotator cuff to bone surface. Typically, two tunnels will be provided, roughly parallel one to the other, in a similar fashion as that used in traditional open surgery for reattaching torn rotator cuffs.

While the preferred embodiment has made reference to shoulder surgery, it is to be understood that the device may be used anywhere that requires the use of either a curved aiming device or a curved receiving device.

Figure 5:
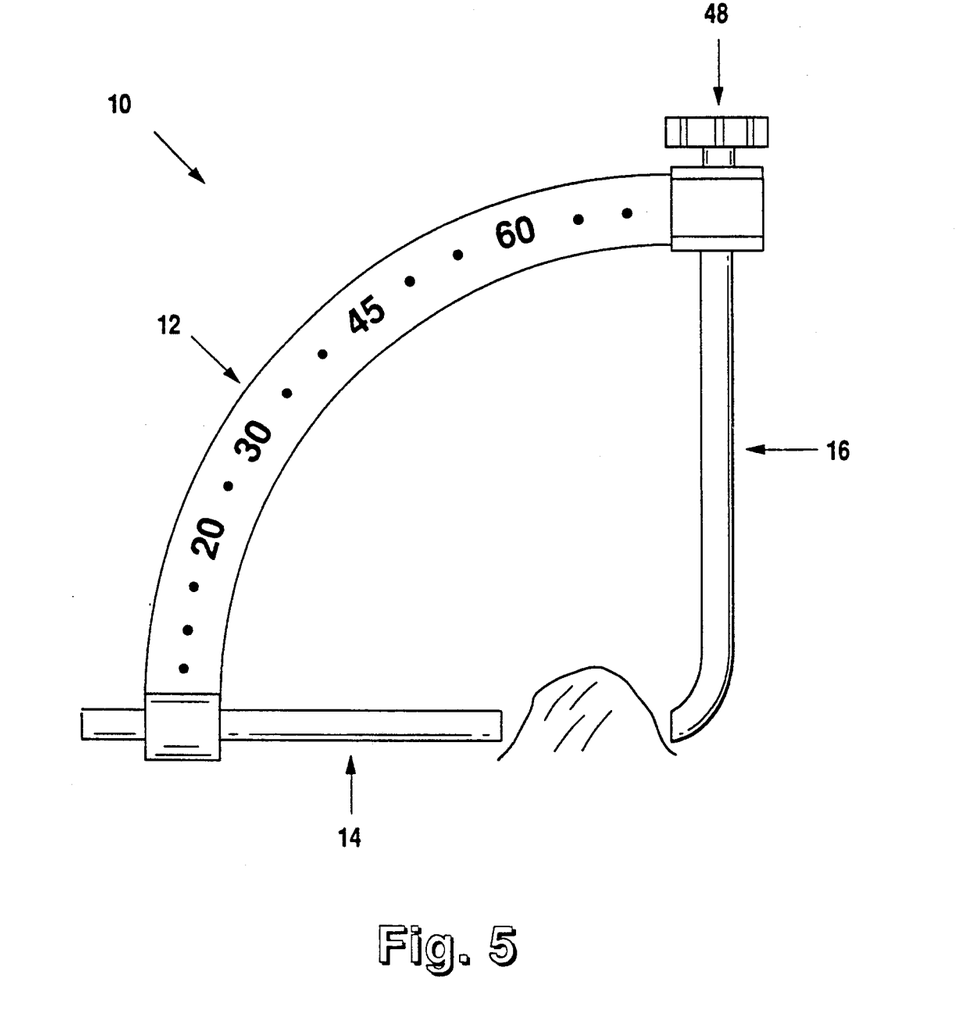
FIG. 5 is a side elevational view of an alternate preferred embodiment of the drill guide.

FIG. 5 illustrates a side elevational view of an alternate preferred embodiment of applicant's drill guide. This particular drill guide 10a provides for an aiming device (14a) which does not have a curved end. That is, the aiming device is capable of receiving a straight needle along its longitudinal axis, which needle will extend out the axis through the bone to be drilled. In this embodiment, the longitudinal axis of the tunnel to be drilled is generally coincident with that aiming device. However, because of obstructions, a curved receiving device (16a) may be required. That is, receiving device (16a) is provided with a curved end (36a) capable of receiving the drill bit (pin) yet deflecting yet it from its straight path through the bone. This will prevent the pin from striking sensitive areas. Of course, it is simply a matter of using receiving device (16a) with curved end (36a) as an aiming device for receipt within straight aiming device (14a). That is, the flexible pin may be inserted through the receiving device which would change its trajectory and allow a straight tunnel to be drilled through a bone along an axis non-aligned with the aiming device, but aligned with the receiving device.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. An orthopedic drill guide device for use in drilling through bone with a flexible pin, comprising:
    a rigid frame with a first end and a second end, said frame having a uniform radius of curvature;
    an elongated, tubular aiming means having a near end rigidly attached near the first end of said frame, said aiming means having a curved removed end for aligning said flexible pin adjacent to an entry point of a bone to be drilled, said aiming means for passage of said flexible pin therethrough;
    an elongated, tubular receiving means adjustably attached to said frame and including means for selectively positioning said receiving means axially about said frame, said receiving means having a near end and having a curved removed end for capturing said flexible pin upon exiting the bone;
    wherein the removed ends of said tubular aiming means and said tubular receiving means are inserted through small incisions in the skin of the patient to points adjacent the bone to be drilled, the tubes of said aiming means and said receiving means having axes nonaligned with the hole drilled in the bone between the removed ends thereof.

2. The device of claim 1 wherein said frame further includes indicia on the surface thereof, the indicia reflecting the angular displacement between said aiming means and said receiving means.

3. The device of claim 1 wherein said receiving means and said aiming means are offset such that they lie, in a common plane, the common plane parallel and offset from the plane of said curved frame.

4. The device of claim 3 wherein the near end of said receiving means includes a hole therethrough for allowing passage of the flexible pin therethrough.

5. The device of claim 1 wherein said aiming means and said frame include a means for selectively adjusting the distance between said frame and the curved removed end of said aiming device.

6. The device of claim 1 wherein said receiving means includes means to adjustably and selectively set the distance between the removed curved end of said receiving means and said frame.

7. The device of claim 1 further including means to releasably remove said receiving device from said frame.

8. The device of claim 1 further including means to releasably unlock said aiming means from said frame.

9. The device as described in claim 1 wherein the positioning means of said receiving means includes a rotatable knob and a friction block for engaging said frame to releasably lock said positioning means to said frame.

10. The device of claim 1 wherein said frame further includes indicia on the surface thereof, the indicia reflecting the angular displacement between said aiming means and said receiving means and wherein said receiving means and said aiming means are offset such that they lie in a common plane, said common plane parallel and adjacent from the plane of said curved frame.

11. The device of claim 1 wherein said frame further includes indicia on the surface thereof, the indicia reflecting the angular displacement between said aiming means and said receiving means and wherein said receiving means and said aiming means have a near end with a hole therethrough for allowing passage of the flexible pin therethrough.

12. The device of claim 1 wherein said frame further includes indicia on the surface thereof, the indicia reflecting an angular displacement between said aiming means and said receiving means and wherein said aiming means includes means for adjustably and selectively adjusting the distance between said frame and the curved, removed end of said aiming device.

13. The device of claim 1 wherein said frame further includes indicia on the surface thereof, the indicia reflecting an angular displacement between said aiming means and said receiving means and wherein said receiving means includes means for adjustably and selectively setting the distance between the removed end of said receiving means and said frame.

14. The device of claim 1 wherein said frame further includes indicia on the surface thereof, the indicia reflecting an angular displacement between said aiming means and said receiving means and wherein said aiming means further includes means to releasably unlock said aiming means for removal from said frame.

15. The device of claim 1 wherein said frame further includes indicia on the surface thereof, the indicia reflecting an angular displacement between said aiming means and said receiving means and wherein said positioning means of said receiving means includes a rotatable knob and friction block for engaging said frame to releasably lock said positioning means to said frame.

16. A method for arthroscopically drilling a tunnel through bone, the method including:

providing a drill guide device having a tubular aiming means with a curved end and a tubular receiving means with a curved end, the aiming means and receiving means attached to a frame for maintaining angular adjustment between the tube of said aiming means and the tube of said receiving means;

determining the entry and exit points at the surface of the bone to be tunneled;

adjusting the drill guide such that the curved ends of said aiming means and said receiving means will lie adjacent to said entry and exit points, respectively, of the tunnel to be drilled; inserting a rotating pin through the aiming device such that it passes through the curved end, through the entry point, through the bone and out at the exit point for receipt into the curved end of the receiving means; and withdrawing the rotating pin from said aiming device.

17. A orthopedic drill guide device for use with a flexible drill bit, comprising:

a rigid frame with a first end and second end, said frame having a uniform radius of curvature; an elongated tubular aiming means;

an elongated tubular receiving means;

said tubular aiming and receiving means being attached to said rigid frame such that they may be set at a preselected angular displacement with respect to one another, either of said aiming means or said receiving means having a curved end removed from said frame, the other of said aiming means or receiving means being straight; wherein said aiming and receiving means have their removed ends placed adjacent to the entry and exit points of the tunnel to be drilled, for receipt and passage therethrough of a rotating flexible drill bit for drilling the tunnel through the bone.

* * * * *